(12) United States Patent
Levy, Jr. et al.

(10) Patent No.: US 6,882,885 B2
(45) Date of Patent: Apr. 19, 2005

(54) HEATING METHOD FOR TISSUE CONTRACTION

(75) Inventors: Stanley Levy, Jr., Saratoga, CA (US); Timothy G. Dietz, Califon, NJ (US)

(73) Assignee: Solarant Medical, Inc., Livermore, CA (US)

( * ) Notice: Subject to any disclaimer, the term of this patent is extended or adjusted under 35 U.S.C. 154(b) by 0 days.

(21) Appl. No.: 10/102,596

(22) Filed: Mar. 19, 2002

(65) Prior Publication Data

US 2003/0181965 A1 Sep. 25, 2003

(51) Int. Cl.⁷ .................................................. A61F 2/00
(52) U.S. Cl. ........................ 607/102; 607/101; 607/113
(58) Field of Search ........................... 607/96–102, 104, 607/105, 113, 116; 606/32, 34, 38, 41, 42, 49, 50

(56) References Cited

U.S. PATENT DOCUMENTS

| | | |
|---|---|---|
| 728,883 A | 5/1903 | Downes |
| 4,679,561 A | 7/1987 | Doss |
| 4,765,331 A | 8/1988 | Petruzzi et al. |
| 5,057,105 A | 10/1991 | Malone et al. |
| 5,201,732 A | 4/1993 | Parins et al. |
| 5,282,799 A | 2/1994 | Rydell |
| 5,423,811 A | 6/1995 | Imran et al. |
| 5,458,596 A | 10/1995 | Lax et al. |
| 5,496,312 A | 3/1996 | Klicek |
| 5,514,130 A | 5/1996 | Baker |
| RE35,330 E | 9/1996 | Malone et al. |
| 5,556,396 A | 9/1996 | Cohen et al. |
| 5,569,242 A | 10/1996 | Lax et al. |
| 5,683,384 A | 11/1997 | Gough et al. |
| 5,853,409 A * | 12/1998 | Swanson et al. .............. 606/31 |
| 5,935,079 A * | 8/1999 | Swanson et al. ............ 600/509 |
| 5,957,920 A * | 9/1999 | Baker .......................... 606/33 |
| 6,035,238 A | 3/2000 | Ingle et al. |
| 6,044,847 A | 4/2000 | Carter et al. |
| 6,063,078 A * | 5/2000 | Wittkampf .................... 606/41 |
| 6,081,749 A | 6/2000 | Ingle et al. |
| 6,091,995 A | 7/2000 | Ingle et al. |
| 6,139,569 A | 10/2000 | Ingle et al. |
| 6,149,647 A * | 11/2000 | Tu et al. ........................ 606/41 |
| 6,156,060 A | 12/2000 | Roy et al. |
| 6,183,468 B1 * | 2/2001 | Swanson et al. .............. 606/40 |
| 6,216,704 B1 | 4/2001 | Ingle et al. |

(Continued)

OTHER PUBLICATIONS

Fulmer, B.R. et al., *Acute and Long–Term Outcomes of Radio Frequency Bladder Neck Suspension*, J. Urology, 167:141–145, (2002).

SURx® Press Release, *SURx® Expands Radio Frequency Product Family with New Transvaginal System for Urinary Incontinence* (Mar. 22, 2002) 2 pages total.

SURx® Press Release, *SURx® Receives FDA Clearance to Market Radio Frequency Bladder Neck Suspension Treatment for Female Urinary Incontinence*(Jan. 29, 2002) 2 pages total.

SURx®, Recent News http;://surx.com/index.cfm-?SCREEN=surx&page=abNews (© 2001) printed from web Aug. 14, 2002, 2 pages total.

*Primary Examiner*—Roy D. Gibson
(74) *Attorney, Agent, or Firm*—Townsend and Townsend and Crew LLP

(57) ABSTRACT

Systems and methods are disclosed for therapeutically heating a target zone of a collagenous support tissue within a patient body. In exemplary embodiments, the present invention provides electronically determining an acceptable or unacceptable contact condition between an energy source and a first tissue layer disposed proximally to the target zone. Upon determining an acceptable contact condition, the target zone is irradiated or otherwise heated for a finite time period with energy. A determination of an unacceptable contact condition causes cessation of irradiating.

65 Claims, 6 Drawing Sheets

U.S. PATENT DOCUMENTS

| | | | |
|---|---|---|---|
| 6,217,574 B1 * | 4/2001 | Webster | 606/41 |
| 6,236,891 B1 | 5/2001 | Ingle et al. | |
| 6,264,653 B1 * | 7/2001 | Falwell | 606/41 |
| 6,273,886 B1 | 8/2001 | Edwards et al. | |
| 6,283,987 B1 | 9/2001 | Laird et al. | |
| 6,292,700 B1 | 9/2001 | Morrison et al. | |
| 6,293,941 B1 | 9/2001 | Strul et al. | |
| 6,322,584 B1 | 11/2001 | Ingle et al. | |
| 6,391,024 B1 * | 5/2002 | Sun et al. | 606/34 |
| 6,413,255 B1 * | 7/2002 | Stern | 606/41 |
| 6,416,504 B1 | 7/2002 | Mosel et al. | |
| 6,461,332 B1 | 10/2002 | Mosel et al. | |
| 2001/0018606 A1 | 8/2001 | Ingle et al. | |
| 2002/0049483 A1 | 4/2002 | Knowlton | |
| 2001/0014819 A1 | 8/2002 | Ingle et al. | |
| 2002/0111586 A1 | 8/2002 | Mosel et al. | |

* cited by examiner

HEATING METHOD FOR TISSUE CONTRACTION

BACKGROUND OF THE INVENTION

1. Field of the Invention

The present invention generally relates to medical devices, methods, and systems. More specifically, the present invention provides techniques for selectively heating and shrinking tissues, particularly for the noninvasive treatment of urinary incontinence and hernias, for cosmetic surgery, and the like.

Urinary incontinence arises in both women and men with varying degrees of severity, and from different causes. In men, the condition occurs almost exclusively as a result of prostatectomies which result in mechanical damage to the sphincter. In women, the condition typically arises after pregnancy where musculoskeletal damage has occurred as a result of inelastic stretching of the structures which support the genitourinary tract. Specifically, pregnancy can result in inelastic stretching of the pelvic floor, the external sphincter, and most often, to the tissue structures which support the bladder and bladder neck region. In each of these cases, urinary leakage typically occurs when a patient's intra-abdominal pressure increases as a result of stress, e.g. coughing, sneezing, laughing, exercise, or the like.

Treatment of urinary incontinence can take a variety of forms. Most simply, the patient can wear absorptive devices or clothing, which is often sufficient for minor leakage events. Alternatively or additionally, patients may undertake exercises intended to strengthen the muscles in the pelvic region, or may attempt behavior modification intended to reduce the incidence of urinary leakage.

In cases where such non-interventional approaches are inadequate or unacceptable, the patient may undergo surgery to correct the problem. A variety of procedures have been developed to correct urinary incontinence in women. Several of these procedures are specifically intended to support the bladder neck region. For example, sutures, straps, or other artificial structures are often looped around the bladder neck and affixed to the pelvis, the endopelvic fascia, the ligaments which support the bladder, or the like. Other procedures involve surgical injections of bulking agents, inflatable balloons, or other elements to mechanically support the bladder neck.

Each of these procedures has associated shortcomings. Surgical operations which involve suturing of the tissue structures supporting the urethra or bladder neck region require great skill and care to achieve the proper level of artificial support. In other words, it is necessary to occlude or support the tissues sufficiently to inhibit urinary leakage, but not so much that intentional voiding is made difficult or impossible. Balloons and other bulking agents which have been inserted can migrate or be absorbed by the body. The presence of such inserts can also be a source of urinary tract infections. Therefore, it would be desirable to provide an improved therapy for urinary incontinence.

A variety of other problems can arise when the support tissues of the body have excessive length. Excessive length of the pelvic support tissues (particularly the ligaments and fascia of the pelvic area) can lead to a variety of ailments including, for example, cystocele, in which a portion of the bladder protrudes into the vagina. Excessive length of the tissues supporting the breast may cause the breasts to sag. Many hernias are the result of a strained, torn, and/or distended containing tissue, which allows some other tissue or organ to protrude beyond its contained position. Cosmetic surgeries are also often performed to decrease the length of support tissues. For example, abdominoplasty (often called a "tummy tuck") is often performed to decrease the circumference of the abdominal wall. The distortion of these support tissues may be due to strain, advanced age, congenital predisposition, or the like.

Unfortunately, many support tissues are difficult to access, and their tough, fibrous nature can complicate their repair. As a result, the therapies now used to improve or enhance the support provided by the ligaments and fascia of the body often involve quite invasive surgical procedures.

For these reasons, it would be desirable to provide improved devices, methods, and systems for treating fascia, tendons, and the other support tissues of the body. It would be particularly desirable to provide improved noninvasive or minimally invasive therapies for these support tissues, especially for the treatment of urinary incontinence in men and women. It would further be desirable to provide treatment methods which made use of the existing support structures of the body, rather than depending on the specific length of an artificial support structure.

2. Description of the Background Art

U.S. Pat. No. 5,423,811 describes a method for RF ablation using a cooled electrode. U.S. Pat. Nos. 5,458,596 and 5,569,242 describe methods and an apparatus for controlled contraction of soft tissue. An RF apparatus for controlled depth ablation of soft tissue is described in U.S. Pat. No. 5,514,130.

U.S. Pat. No. 4,679,561 describes an implantable apparatus for localized heating of tissue, while U.S. Pat. No. 4,765,331 describes an electrosurgical device with a treatment arc of less than 360 degrees. An impedance and temperature generator control is described in U.S. Pat. No. 5,496,312. Bipolar surgical devices are described in U.S. Pat. Nos. 5,282,799, 5,201,732, and 728,883.

BRIEF SUMMARY OF THE INVENTION

The present invention provides, systems, methods, and software modules for controlling the delivery of a therapeutic energy that can heat and strengthen a target zone of a collagenous support tissue within a patient body.

The method and systems of the present invention allow a user to determine if the applicator, typically having a plurality of electrodes, is in an acceptable contact condition with the tissue. If the electrode surfaces do not substantially uniformly contact the tissue surface, a target tissue zone may not be heated adequately and the proximal tissue interposed between the electrodes and target tissue zone may not be adequately cooled and protected. This may cause inadequate treatment of the target tissue zone and unintended treatment of the proximal tissue.

In exemplary embodiments, the user can determine if there is an acceptable contact condition by measuring various impedance levels between the electrodes and the tissue that is contacted. In one configuration, a tissue impedance is individually measured with the electrodes and the measured impedance are compared to determine if there is a substantially uniform contact between the electrodes and the tissue. If the measured impedance levels are within a predetermined range from each other, it is determined that there is a sufficiently uniform contact between the electrodes and the proximal tissue.

In another configuration, the tissue impedance is measured with the individual electrodes and compared to a maximum impedance level. If the measured tissue impedance levels are below the maximum impedance level, it is determined that there is a sufficiently uniform contact between the electrodes and the proximal tissue and the treatment of the target zone is allowed to commence.

In exemplary embodiments, the methods of the present invention comprises electronically determining an acceptable or unacceptable contact condition between an energy source and a first tissue layer disposed proximally to the target zone. Upon determining an acceptable contact condition, the target zone is irradiated for a finite time period (e.g., a predetermined maximum time limit) with energy. A determination of an unacceptable contact condition causes prevention or cessation of irradiating.

In another aspect, the present invention provides a computer system. The computer system includes a memory coupled to a processor. The memory can be configured to store a plurality of code modules for execution by the processor. The plurality of code modules include a code module for determining if there is an acceptable or unacceptable contact condition between an energy source and a first tissue layer disposed proximally to a target zone of a collagenous support tissue within a patient body. A code module can initiate irradiation for a finite time period of the target zone upon determining the acceptable contact condition. Finally, a code module can cause prevention or cessation of the irradiating when the unacceptable contact condition is determined.

In another aspect of the present invention, a system is disclosed for therapeutically strengthening a target zone of a collagenous support tissue within a patient body. In exemplary embodiments, the system comprises a processor and an applicator operably coupled to the processor. The applicator can be adapted to establish an acceptable or unacceptable contact condition with a first tissue layer disposed proximally to the target zone. The processor is adapted to determine the contact condition. The applicator is further adapted to irradiate the target zone with energy for a finite time period upon a determination by the processor of an acceptable contact condition. The processor is further adapted to cause cessation of the irradiating upon determining an unacceptable contact condition.

In a further aspect, the present invention provides a system for therapeutically strengthening a target zone of a collagenous support tissue within a patient body. The system comprises an applicator having a plurality of electrodes adapted to establish an acceptable or unacceptable contact condition between the plurality of electrodes and a first tissue layer disposed proximally to the target zone. A controller is operably coupled to the applicator to control the delivery of energy through the electrodes on the applicator. The controller is configured to move between a first mode, a second mode and a third mode. In the first mode, the controller can determine if there is an acceptable contact condition between the plurality of electrodes and the first tissue layer.

If the controller determines that there is an acceptable contact condition, the controller moves to the second mode and causes the plurality of electrodes to heat the target zone for a finite time period. If the controller determines there is unacceptable contact condition between the applicator and tissue, the controller stays in the first mode until acceptable contact is made. If however, the controller had moved to the second mode and the controller thereafter determines that there is unacceptable contact, the controller moves to the third mode to cause cessation of the heating of the target zone.

In yet another aspect, the present invention provides a method of heating a target tissue. The method comprises placing an applicator against a first tissue that is adjacent the target tissue. Energy is delivered to the target tissue to heat the target tissue. A temperature rate of change of the target tissue is continuously measured to determine if a temperature equilibrium condition in the target tissue has been reached. If the equilibrium condition is reached, the delivery of energy is adjusted. If the equilibrium condition is not reached the delivery of energy to the target tissue is continued, until the equilibrium condition is reached.

In a further aspect, the present invention provides a method of therapeutically heating a target zone of a collagenous tissue within a patient body. The method comprises continuously monitoring a contact condition between a tissue layer and a plurality of electrodes A heating energy is delivered with the plurality of electrodes to heat the target zone. The delivering of the heating energy to the target zone is automatically adjusted if an acceptable contact condition between the tissue layer and the at least one electrode is not maintained.

The above aspects and other aspects of the present invention may be more fully understood from the following detailed description, taken together with the accompanying drawings.

DESCRIPTION OF THE PREFERRED EMBODIMENT

Figure 1:
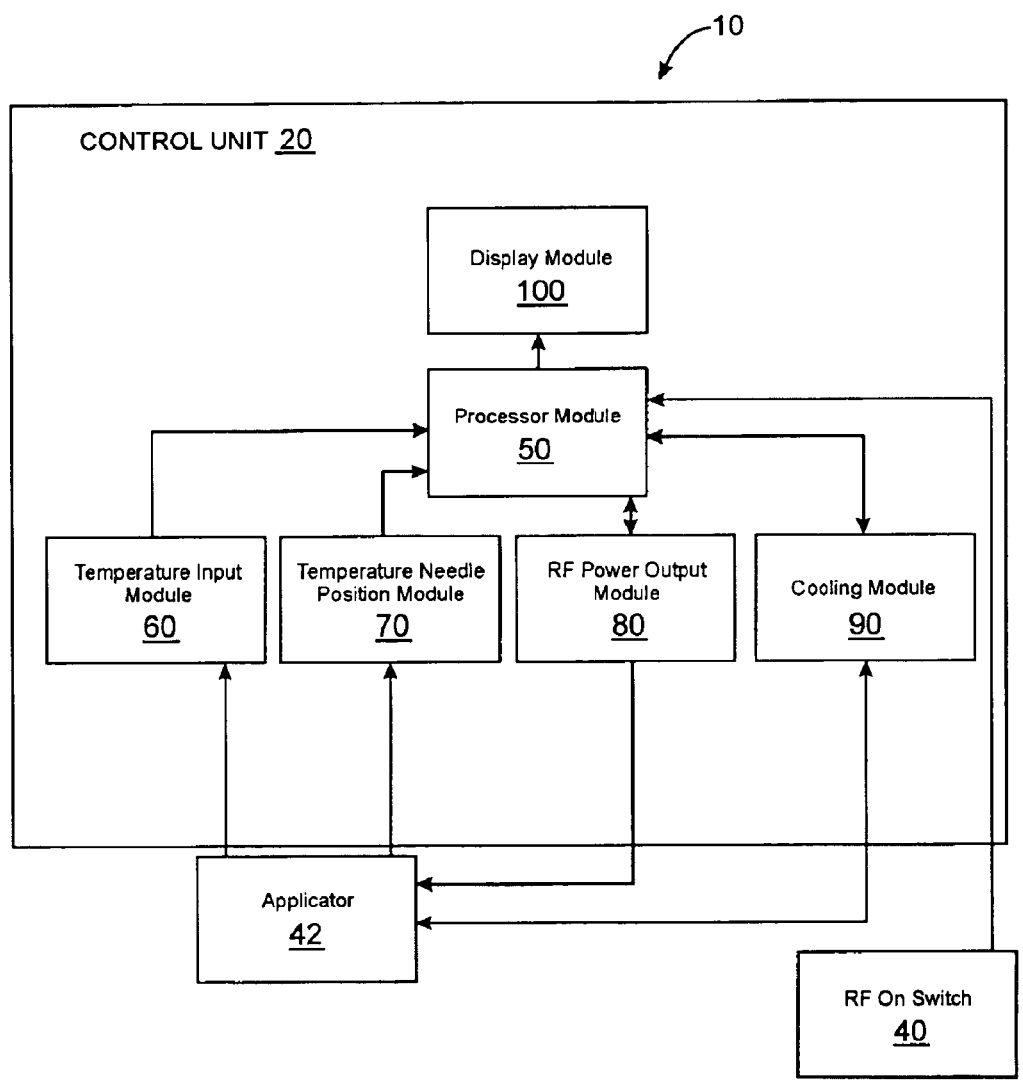
FIG. 1 is a block diagram of a system incorporating principles of the present invention.

The present invention is directed to inducing controlled stiffening, contraction, or shrinkage of a support tissue of the body, typically being a collagenous tissue such as fascia, ligament, or the like. For treatment of urinary incontinence, the tissue structure will be one that is responsible in some manner for control of urination, or for supporting a such a tissue. Exemplary tissue structures include the urethral wall, the bladder neck, the bladder, the urethra, bladder suspension ligaments, the sphincter, pelvic ligaments, pelvic floor muscles, fascia, and the like. Treatment of other conditions may be effected by selective shrinking or stiffening of a wide variety of other tissues, including (but not limited to) the diaphragm, the abdominal wall, the breast supporting ligaments, the fascia and ligaments of the joints, the collagenous tissues of the skin, and the like. Related devices, methods, and system are also described in co-pending U.S. patent application Ser. No. 09/229,508, filed Jan. 12, 1999, the full disclosure of which is incorporated herein by reference.

Tissue contraction or stiffening results from controlled heating of the tissue by affecting the collagen molecules of the tissue. Contraction occurs as a result of heat-induced uncoiling and repositioning of the collagen β-pleated structure. By maintaining the times and temperatures set forth below, significant tissue contraction can be achieved without substantial collateral tissue necrosis. Stiffening results from the loss of elasticity of the tissue due to the formation of scar tissue and/or attachment of adjacent support tissues to each other as a result of controlled heating of the tissue.

The temperature of the target tissue structure will generally be raised to a value in the range from about 60° C. to 110° C., often being in the range from about 60° C. to 80° C., preferably in the rang from about 65° C. to 75° C., and will generally effect a shrinkage of the target tissue in at least one dimension of between about 15 and 50 percent. Alternatively, the temperature of the target tissue structure will generally be raised to value in the range of 45° C. to 60° C. and will generally effect stiffening of the target tissue. The rise in temperature may be quite fast, although there will often be advantages in heating tissues more slowly, as this will allow sufficient heat to be removed from tissues which are not targeted for therapy, thereby minimizing collateral damage. However, if too little heating energy is absorbed by the tissue, blood perfusion will transfer the heat away from the targeted tissue, so that the temperature will not rise sufficiently to effect therapy.

The total amount of energy delivered will depend in part on which tissue structure is being treated, how much tissue is disposed between the target tissue and the heating element, and the specific temperature and time selected for the protocol. The power delivered will often be in the range from 10 W to 100 W, usually being about 30 W. The temperature will usually not drop instantaneously when the heating energy stops, so that the tissue may remain at or near the therapy temperature for a time from about 10 seconds to about 2 minutes, and will often cool gradually back to body temperature.

While the remaining description is generally directed to a system for treatment of urinary stress incontinence of a female patient, it will be appreciated that the present invention will find many other applications for selectively directing therapeutic heating energy into the tissues of a patient body for shrinking of tissues, for ablation of tissues and tumors, and the like.

FIG. 1 is a block diagram of a system 10 incorporating principles of the present invention. System 10 generally comprises a control unit (controller) 20 functionally coupled with an applicator 42 and a switch 40 serving to activate and deactivate transmission of RF energy by applicator 42. Processor 50 has associated therewith a memory (not shown) adapted to store software code instructions to operate the modules in the control unit, including temperature input module 60, temperature needle position module 70, RF power output module 80, cooling module 90 and display module 100. Display module 100 is of a type known in the art. Display module 100 cooperates with processor 50 in order to provide status and error messages pertaining to each step of the process described below in further detail.

Figure 2:
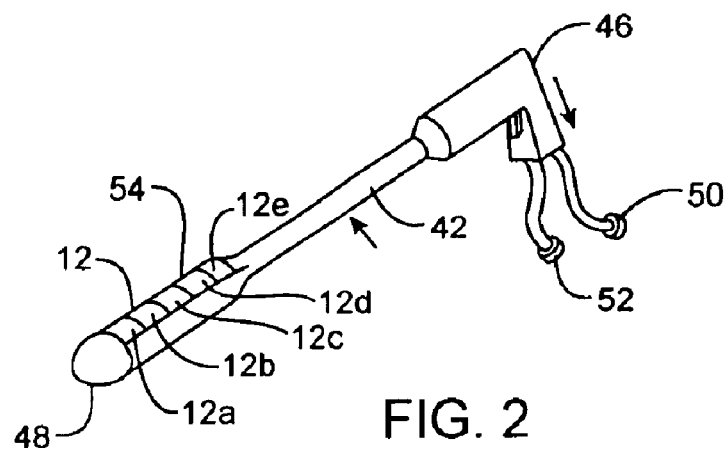
FIG. 2 is a perspective view an applicator employed during implementation of principles of the present invention.

FIG. 2 is a perspective view of the preferred embodiment of applicator 42. Applicator 42 has a proximal end 46 and a distal end 48. Electrode 12 (including segments 12a, 12b, 12c, 12d, and 12e) is mounted near the distal end 48 of applicator 42. Applicator 42 preferably has a diameter of between about 2 and 4 cm, and a shaft length of between about 6 and 12 cm. An electrical coupling 50 is coupleable to RF power output module 80 of controller 20. A fluid coupling 52 provides attachment to cooling module 90 of controller 20. Cooling fluid may be recycled through applicator 42, so that more than one fluid coupling may be provided.

The segments of electrode 12 are quite close to each other, and preferably define a substantially flat electrode surface 54. The cooling fluid flows immediately below surface 54, the surface material preferably being both thermally and electrically conductive. Ideally, surface 54 is as large as the tissue region to be treated, and a thermocouple or other temperature sensor may be mounted adjacent the surface for engaging the tissue surface and measuring the temperature of the engaged tissue.

In a preferred embodiment, a temperature probe (not shown) is attached to applicator 42 and deployed into a patient tissue target zone, further discussed below. The temperature probe is a metal needle with one or more thermocouples located at the needle tip. The needle is designed to penetrate tissue to place the thermocouples in the tissue target zone. Alternatively, the temperature probe can be separate from applicator 42. In either case, the temperature probe is operably coupled to temperature input module 60.

Figure 3:
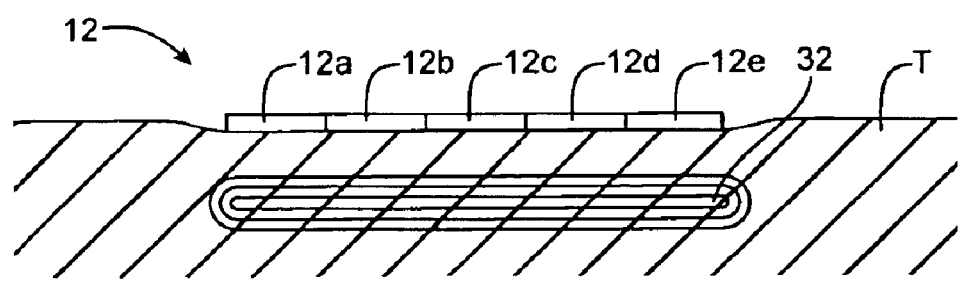
FIG. 3 schematically illustrates the positioning of an electrode of the applicator of FIG. 2 relative to patient tissue.

FIG. 3 schematically illustrates the positioning of electrode 12 relative to patient tissue during implementation of principles of the present invention. As seen therein, electrode 12 is disposed so as to contact a tissue layer T of a patient body at a position proximal to a target zone 32 within the patient body for which strengthening is desired. Specifically, each of segments 12a, 12b, 12c, 12d and 12e is adapted to contact a corresponding region, disposed between each such segment and target zone 32, of tissue layer T.

Figure 4:
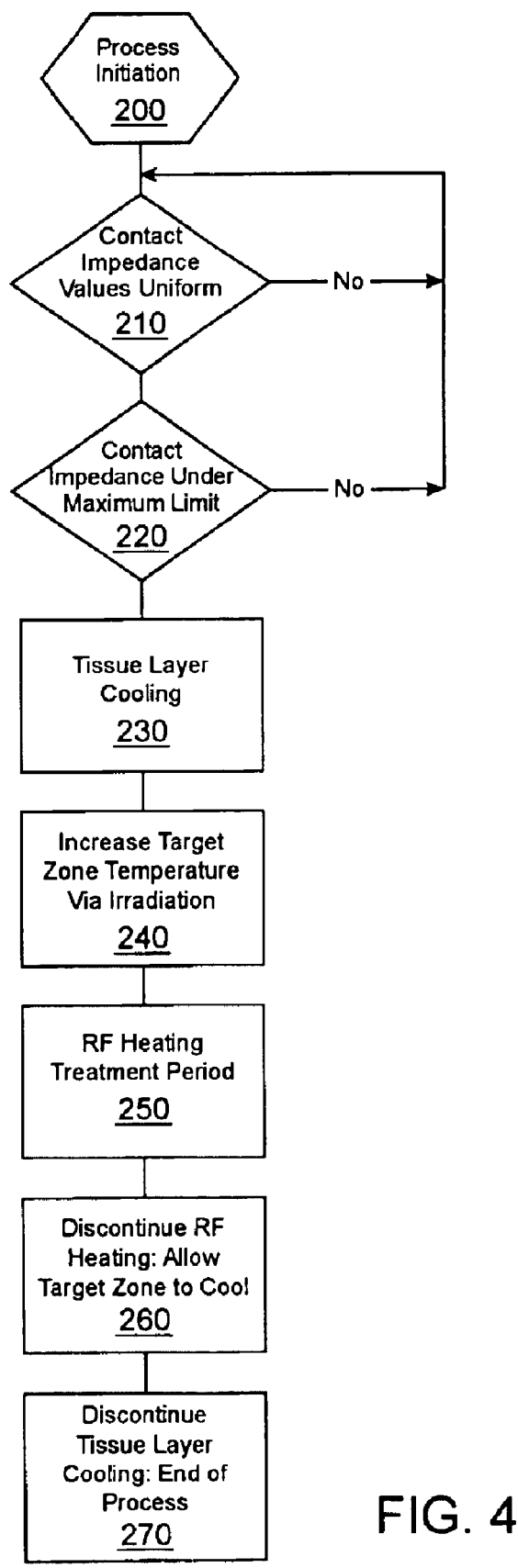
FIG. 4 is a flow diagram illustrating the process through which principles of the present invention are employed in the strengthening process.

FIG. 4 is a flow diagram illustrating the process through which principles of the present invention are employed in tissue strengthening/contraction/stiffening. At step 200, the user activates a power activation switch (not shown) of controller 20. In response to switch activation, processor 50 performs a diagnostic self test while displaying on display unit 100 a system test message showing the progress of the tests. If any component of controller 20 fails the test, an error code and a description of the failure shall be displayed on display unit 100. If the diagnostic self test indicates no such error, processor 50 shall provide a message to display unit 100 indicating that the cooling system 90 is coming down to a predetermined cool-down temperature. This message may further indicate the current temperature of and estimated time to predetermined cool-down temperature of the cooling system 90.

Additionally, if the diagnostic self test indicates no such error, processor 50 shall provide a message to display unit 100 indicating that controller 20 is ready for attachment of applicator 42 thereto. Processor 50 may also determine whether applicator 42 is operably compatible with controller 20. Processor 50 may further cause display unit 100 to display the status of such compatibility, including any associated error messages. Processor 50 continually monitors the cooling system 90 and causes display of cooling system status.

Once applicator 42 is connected to controller 20, processor 50 initiates a system test of applicator 42. Such applicator test may include processor 50, via display unit 100, prompting the user to advance the temperature probe into air, retract the temperature probe from air, and/or press a footswitch 40 coupled to controller 20 to activate the delivery of RF energy to the applicator electrode 12. Processor 50 determines the temperature probe advance or retract state by comparing measured temperature values to predetermined values that correlate to the temperature of a cooled electrode 12 or the temperature of air in a typical setting. Processor 50 monitors the RF voltage and current values to verify through electrical impedance calculations that electrical continuity exists to the individual elements of electrode 12. Processor 50 determines continuity status by comparing calculated impedance values to predetermined values that correlate to continuous or broken electrical connections to the electrode segments. At the conclusion of the applicator test, and assuming no errors are indicated, processor 50 generates a message to display unit 100 indicating ready-for-placement status of applicator 42. Otherwise an error message shall be displayed. The process then moves to step 210.

At steps 210 and 220, an acceptable or unacceptable contact condition between electrode 12 and tissue layer T is electronically determined. If the cooled electrode surface does not uniformly contact the tissue surface, the target tissue zone may not be heated adequately and the proximal tissue T interposed between the electrode and target tissue may not be adequately cooled. This may cause inadequate treatment of the target tissue and unintended treatment of the proximal tissue. The user places the applicator such that electrode 12 contacts the tissue layer proximal to the target zone. The temperature probe is not deployed into the target tissue so that the applicator may be freely repositioned if necessary. Stepping on the footswitch will cause each segment of electrode 12 to irradiate with energy at a first power level each corresponding region of tissue layer T. Preferably, this first power level is approximately 5 watts and is such that no tissue heating is effected. Controller 20 applies RF energy alternately between the center electrode segment 12c and either the distal electrode segments 12a, 12e or proximal electrode segments 12b, 12d. Preferably, such energy switching from one electrode segment to another occurs approximately every three seconds, but may switch more rapidly to acquire contact condition information more quickly.

At step 210, uniformity of electrode contact can be determined by comparing the difference in tissue electrical impedance measured between the distal/center and proximal/center segments. Tissue contact impedance is measured as the RF is switched from the distal to proximal electrode segments and vice versa after a predetermined time of irradiating the tissue. The maximum impedance difference between the distal and proximal electrode segments is defined as the Tissue Impedance Modulation (TIM). TIM can be computed by processor 50. Preferably, a TIM of greater than 20Ω shall result in processor 50 providing a message to display unit 100 warning that the electrode contact to the tissue is unacceptable. A TIM greater than approximately 14Ω to 20Ω shall result in processor 50 providing a message to display unit 100 warning that the electrode contact to the tissue is marginal but acceptable. A TIM of 14Ω or less shall result in processor 50 providing a message to display unit 100 indicating that the electrode contact to the tissue is acceptable. It should be appreciated however, that the above impedance values are merely examples, and that the impedance values may be adjusted for different tissues and electrode geometries. For example, instead of having the TIM threshold as 20Ω, the TIM can threshold can be anywhere between a range of about 15Ω and 30Ω, or more. The display of TIM may also be done graphically such as the position of a bar denoting the TIM value and/or encoded by color such as red for unacceptable, yellow for marginal, and green for acceptable.

As well, if the cooled electrode surface contacts the tissue surface uniformly but with inadequate force, the target tissue zone may not be heated adequately and the proximal tissue T interposed between the electrode and target tissue may not be adequately cooled. This may cause inadequate treatment of the target tissue and unintended treatment of the proximal tissue. At step 220, processor 50 can determine acceptable contact force by measuring the maximum impedance of both the distal and proximal electrode sets. Preferably, if the maximum impedance exceeds a typical value of between a range of 200Ω to 400Ω, the processor 50 shall provide a message to display unit 100 warning that the electrode contact to the tissue is unacceptable. The maximum acceptable value may range from 200Ω to 400Ω, depending upon tissue type and electrode geometries.

It should be appreciated that in other exemplary embodiments, if the maximum impedance value exceeds a predetermined value or if the TIM exceeds a predetermined value, instead of a displaying a warning on display unit 100, the processor may prevent the processor from moving on to the next step.

In exemplary embodiments, TIM and the maximum impedance values will both be measured. It should be appreciated however, that in alternative embodiments, only one of TIM and the maximum impedance values will be measured.

Upon determining an acceptable contact condition, the user deploys the temperature probe into the tissue. At step 230, tissue is cooled by the fluid cooling system of applicator 42 so as to cause the temperature of target zone 32 to remain below a first predetermined temperature. Cooling the tissue prior to application of heating energy lowers the temperature of tissue adjacent to the target zone so as to minimize heating of this adjacent tissue due to thermal conduction from the target tissue zone as the target tissue 32 is heated due to resistance to current flow by directed application of RF energy to the target zone tissue 32. Processor 50 receives the temperature of the target zone 32 as provided by the temperature probe and monitors the progress of cooling. Target zone temperature information is sent by processor 50 to display module 100. When the tissue zone 32 has dropped to a pretreatment cool-down temperature of, preferably, 30° C. or less (but may range from 25° C. to 35° C., processor 50 generates to display unit 100 a message advising the user that RF treatment energy may be applied to target zone 32. Processor 50 will prevent RF treatment energy from being applied until the pretreatment cool-down temperature has been reached. It should be appreciated, however, that this pre-heat treatment cooling may be optional, depending upon application such as tissue type, desired treatment temperature, treatment time, and the like.

In turn, at step 240, the target zone 32 is irradiated by electrode 12 for a finite time period with RF energy so as to increase the temperature of target zone 32. When the user activates the RF on switch 40, processor 50 applies the RF power in two stages. First, processor 50 applies initial RF power (of, preferably, 20 watts +5 watts) for a fixed amount of time, (preferably 25 seconds ±5 seconds) and confirms acceptable contact between applicator 42 and tissue layer T. The value for initial RF power and time of application are selected to provide minimal tissue heating so as to reduce the likelihood of overheating non-target tissue in the event of unacceptable tissue contact. Contact quality information is shown on display module 100. The user may make use of this information to attempt to improve contact quality if unacceptable or marginal. If at the end of this time period, contact is unacceptable, RF energy application will cease. If contact is acceptable, processor 50 then applies treatment RF power (of, preferably, 40±10 watts), and continues to monitor the tissue temperature as described in step 250. Processor 50 shall monitor contact condition throughout the treatment. If contact becomes unacceptable during treatment, RF power shall be turned off automatically via a signal generated by processor module 50. It should be appreciated however, that in alternative embodiments, instead of turning off the RF power, the RF power may be reduced to a lower power level, until uniformity of contact is again achieved. The lower power level may or may not cause the first tissue layer to be heated.

Figure 5:
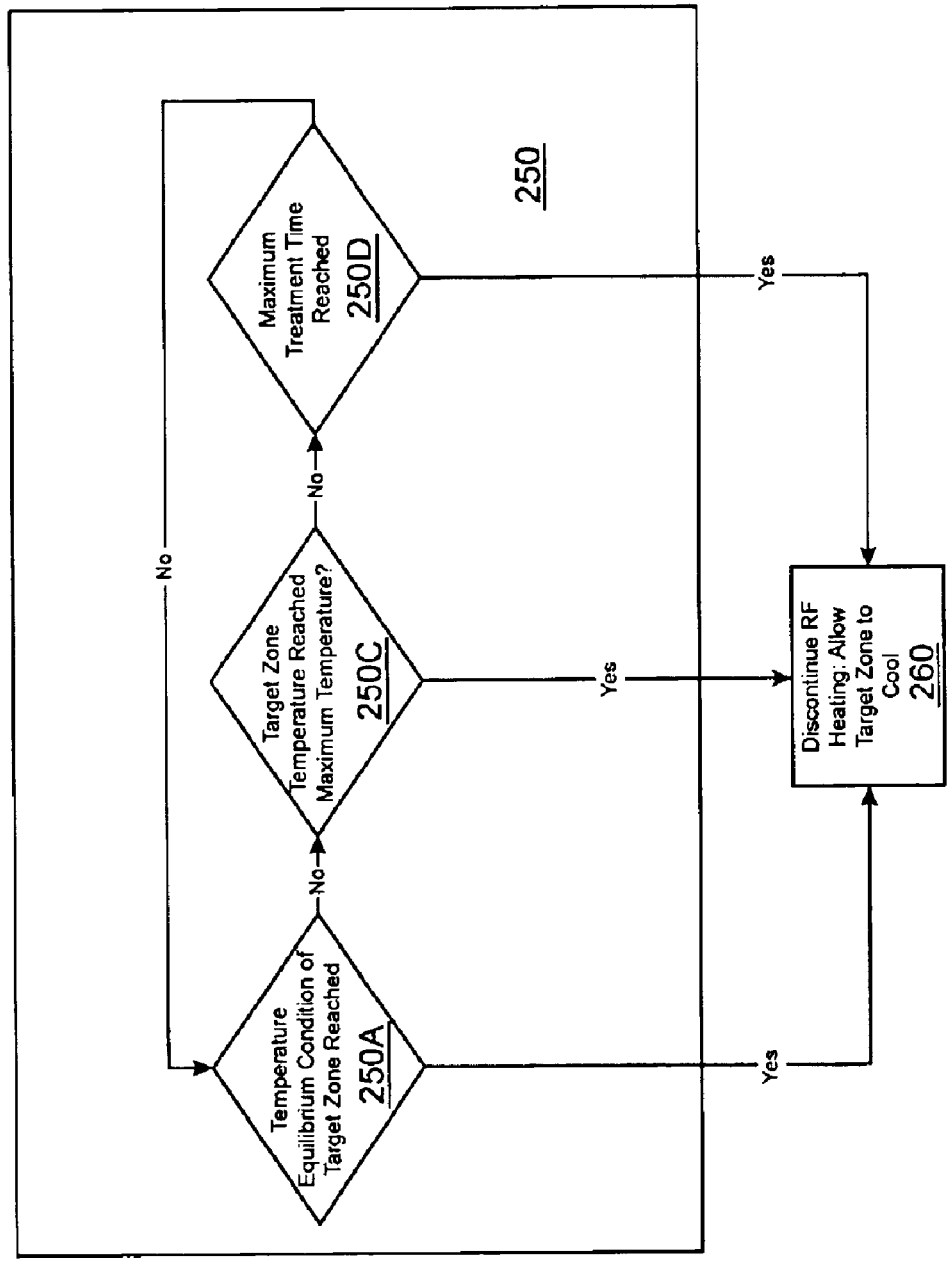
FIG. 5 is a flow diagram illustrating in further detail step 250 of the flow diagram of FIG. 4.

The user can turn off the RF power at anytime by deactivating the RF ON switch 40. The user may pause treatment for, preferably, two to four seconds. Within this time, the user may resume treatment by reactivating RF on switch 40; otherwise, processor 50 shall disable RF treatment power and proceed to step 260. At step 250, and as better illustrated in FIG. 5, the second stage RF heating treatment period occurs. At step 250A a temperature equilibrium condition of the target zone 32 is determined. This temperature equilibrium condition occurs when the temperature rate of change of the target zone 32 descends below a predetermined rate change level (preferably, 0.03–0.07° C./second) and remains below this level for a predetermined time period, (preferably, 20–60 seconds). If such equilibrium condition exists, the process moves to step 260.

If, at step 250A, no such equilibrium condition is determined to exist, the process moves to step 250C. At step 250C, a determination is made as to whether target zone 32 has reached a predetermined maximum temperature, typically between approximately 60° C. and 80° C., and preferably between approximately 65° C.–75° C. If such temperature has been reached, the process moves to step 260. If this maximum temperature has not been reached, the process moves to step 250D.

At step 250D if the total elapsed time of RF energy application reaches the maximum treatment time (of, preferably, 150–200 seconds), the process moves to step 260. Otherwise, the process moves back to step 250A.

Figure 6:
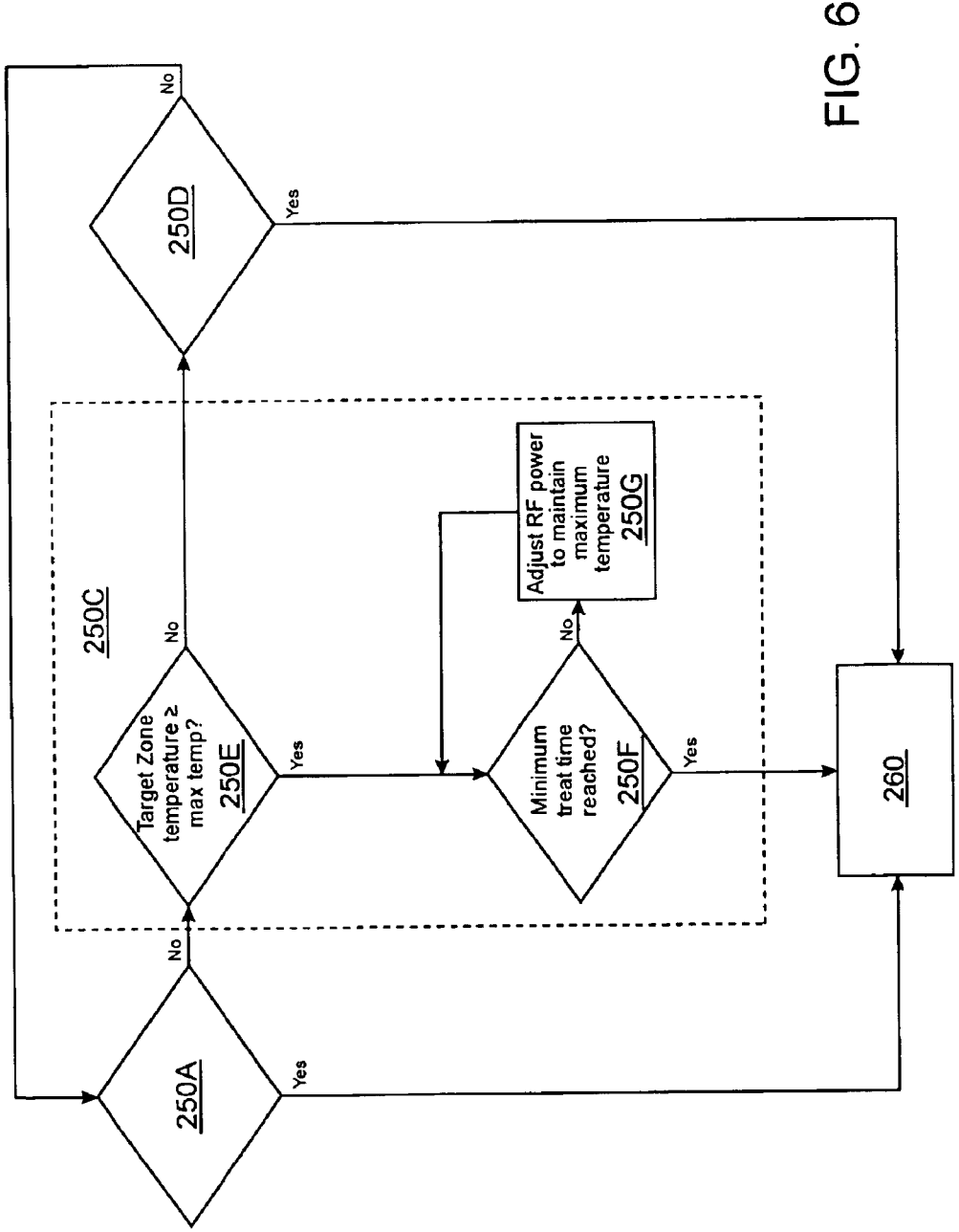
FIG. 6 shows an alternative embodiment of step 250C of the flow diagram of FIG. 5.

An alternative embodiment of step 250C is shown in FIG. 6. It may be desirable to ensure a minimum amount of tissue heating time (preferably 20–60 seconds) at or near the target temperature. At step 250E, a determination is made as to whether target zone 32 has reached a predetermined maximum temperature, typically between approximately 60° C. and 80° C., and preferably between approximately 65°–75° C. If such temperature has been reached, the process moves to step 250F. If a minimum treatment time (preferably 90–150 seconds) has been reached, the process moves to step 260. If such a time has not been reached, the process moves to step 250G where the RF power is adjusted initially downward and then upward or downward as needed by processor 50 to maintain the tissue temperature at the maximum temperature value. The process returns to step 250F and this loop is repeated until the minimum treatment time is reached.

Figure 7:
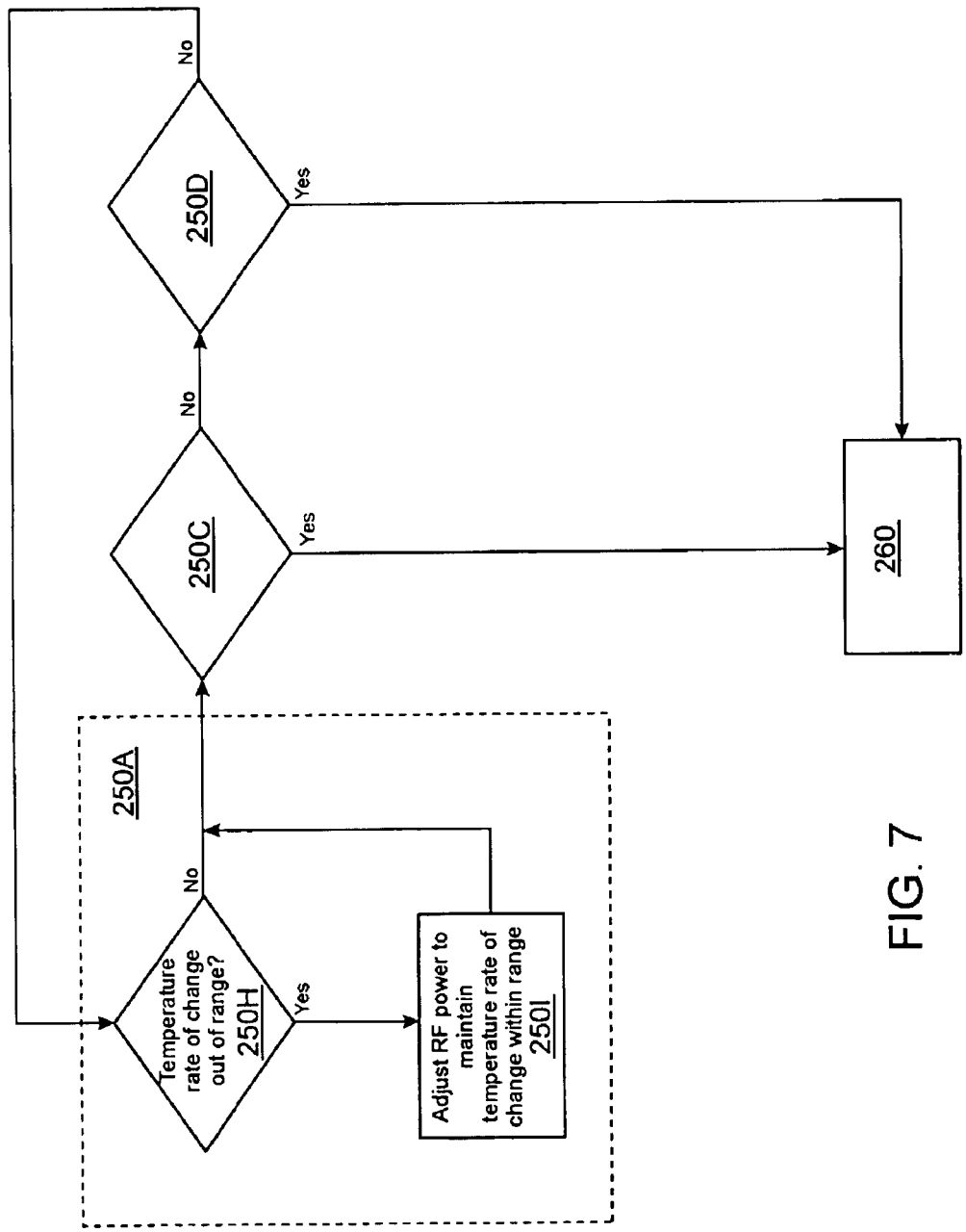
FIG. 7 shows an alternative embodiment of step 250A of the flow diagram of FIG. 5.

An alternative embodiment of step 250A is shown in FIG. 7. It may be desirable to adjust the RF power to control the rate of tissue heating so that the target zone tissue reaches the desired maximum temperature, typically between approximately 60° C. and 80° C., and preferably between approximately 65° C.–75° C., in the desired range of treatment time (preferably, 90–150 seconds). At step 250H, a determination is made as to whether the temperature rate of change of the target zone 32 is within a predetermined range of rate change levels (preferably, 0.2–0.6° C./second). If in such a range, then the process moves to step 250C. If the temperature rate of change is not within the predetermined range, the process moves to step 250I where the RF power is adjusted upward or downward as needed by processor 50 to maintain the tissue temperature rate of change within the predetermined range. The process then moves to step 250C.

At step 260, RF irradiation is discontinued and target zone 32 is cooled to a third predetermined temperature (preferably, 30–50° C.). Cooling of the target and adjacent tissues after heating minimizes the undesirable additional heating of adjacent tissues due to thermal conduction from the target zone tissue 32. Upon target zone 32 reaching this third temperature, at step 270, cooling of the tissue is discontinued, thus ending the round of treatment. It should be appreciated however, that the post heating cool down cycle is optional, depending upon application such as tissue type, desired treatment temperature, treatment time, and the like.

According to principles of the preferred embodiment of the present invention, the above-described treatment process is such that the user is relieved of any controls or adjustments that can be performed automatically by system 10. The user turns the RF power on and off and deploys and retracts the temperature probe. Processor 50 maintains the proper power level, monitors the above-described treatment parameters, prompts the user, and displays status messages, alerts/warnings and error conditions. These functions, including all associated with the inventive process described above, are typically initiated and/or performed by the above-referenced software code stored in a memory of and executing on processor 50.

According to principles of the present invention, processor 50 continually samples and stores the parameters listed below at a minimum of 10 samples per second. These treatment parameters have ranges that can be set by users of system 10.

The treatment parameters include RF voltage. Processor 50 reads the root mean squared value of the applied RF voltage. The voltage scale will preferably range from zero to 120 volts root mean squared.

The treatment parameters include RF current. Processor 50 reads the root mean squared value of the applied RF current. The current scale will preferably range from zero to 2 amperes root mean squared.

The treatment parameters include impedance. Processor 50 computes the impedance from the root mean squared voltage and current. Such calculation is performed at least two times per second. The impedance scale will preferably range from 10 to 300Ω.

The treatment parameters include RF power. Processor 50 computes the RMS power from the root mean squared voltage and current. Such calculation is performed at least two times per second. The power scale will preferably range from zero to 50 watts.

The treatment parameters include treatment time. Processor 50 monitors the treatment time. The time scale will preferably range from 0 to 300 seconds.

The treatment parameters include tissue temperature. Processor 50 reads the temperature of the tissue under treatment as provided by the temperature probe. This temperature scale will preferably range from zero to 100° C.

The treatment parameters include coolant flow status indicator. Processor 50 monitors the coolant flow rate status signal, and displays an error message if a flow alarm is received from the cooler subsystem.

The treatment parameters include coolant temperature. Processor 50 reads the value of the coolant temperature. This temperature scale will preferably range from −5° C. to 40° C.

According to principles of the present invention, processor 50 identifies and displays appropriate error messages pertaining to the following conditions: cooling system does not reach appropriate temperature in prescribed time, coolant flow rate out of range, coolant conductivity out of range, and errors encountered during the diagnostic system tests. Processor 50 allows the user to set date and time, audio tone level, and language selection for display on display unit 100. Processor 50 generates audio tones to prompt the user for actions and to indicate error and out of range conditions. A continuous or intermittent audio tone shall be emitted by a speaker (not shown) associated with processor 50 at a steady rate when RF energy is applied. Processor 50 generates to display 100 a welcome screen showing a logo or other graphics desired by user of system 10. Processor 50 displays recoverable error condition messages and prompts the user to correct the cause. Unrecoverable error messages shall display on display unit 100 and give appropriate error information.

Control unit 20 completes a self-test each time the power is turned on. Control unit 20 allows processor 50 to complete its internal tests and display error messages accordingly. A fault in the RF output test can be diagnosed and displayed as an error condition. Processor 50 provides a clock signal for hardware detection of software operation. Processor 50 performs tests of internal subsystems, including but not limited to the analog and digital electronics. Control unit 20 provides a special test, diagnostics and service mode, which will allow the manufacturer or servicer of system 10 to bypass the normal diagnostic self-tests, be able to manually execute all functions and perform calibration and setup. This mode is generally not be accessible to the user.

Although the invention has been described in terms of the illustrative embodiment, it will be appreciated by those skilled in the art that various changes and modifications may be made to the illustrative embodiment without departing from the spirit or scope of the invention. It is intended that the scope of the invention not be limited in any way to the illustrative embodiment shown and described but that the invention be limited only by the claims appended hereto.

What is claimed is:

1. A method of treating incontinence by heating a target support tissue, the method comprising:
   placing an applicator adjacent a first tissue layer that is adjacent the target support tissue;
   delivering energy from the applicator to heat the target support tissue; and
   substantially continuously measuring a temperature rate of change of the target support tissue to determine if a target temperature equilibrium condition in the target support tissue has been reached.

2. The method of claim 1 wherein if the target temperature equilibrium condition is reached, the method comprises adjusting the delivering energy to the target support tissue, and if the target temperature equilibrium condition is not reached, the method comprises continuing the delivery of energy to the target support tissue until the target temperature equilibrium condition is reached.

3. The method of claim 1 wherein the target temperature equilibrium condition is a temperature rate of change below approximately 0.07° C./second.

4. The method of claim 2 comprising discontinuing the delivering of energy to the target support tissue if the temperature rate of change reaches the target temperature equilibrium condition in a predetermined time.

5. The method of claim 1 comprising increasing the delivery of energy to a level that maintains the temperature rate of change above the target temperature equilibrium condition.

6. The method of claim 1 wherein the target temperature equilibrium condition comprises a temperature rate of change of between approximately 0.2° C./second to 0.6° C./second.

7. The method of claim 6 comprising reducing the delivery of energy to the target support tissue if the temperature rate of change goes above the target temperature equilibrium condition.

8. The method of claim 6 comprising increasing the delivery of energy to the target support tissue if the temperature rate of change goes below the target temperature equilibrium condition.

9. The method of claim 1 comprising determining if the target target tissue has reached a maximum temperature,
   wherein if the maximum temperature has been reached, adjusting the delivery of energy.

10. The method of claim 9 wherein adjusting the delivery of energy comprises discontinuing the delivery of energy.

11. The method of claim 9 comprising determining if a minimum treatment time has been reached, and
    wherein if the minimum treatment time has not been reached, adjusting the delivery of energy comprises reducing the delivery of energy to maintain the maximum temperature.

12. The method of claim 1 comprising determining if a maximum treatment time has been reached, wherein if the maximum treatment time has been reached delivering energy is automatically discontinued.

13. The method of claim 1 comprising precooling the first tissue layer.

14. The method of claim 1 comprising cooling the first tissue layer and target support tissue after delivering energy.

15. A method of therapeutically heating a target zone of a collagenous tissue within a patient body, the method comprising:
    continuously monitoring a contact condition between a tissue layer and a plurality of electrodes;
    delivering a heating energy with the plurality of electrodes to heat the target zone;
    precooling at least one of the target zone and the tissue layer prior to delivering the heating energy; and
    automatically adjusting the delivering of the heating energy to the target zone if an acceptable contact condition between the tissue layer and at least one electrode is not maintained; and
    monitoring a temperature rate of change in the target zone and automatically discontinuing the delivering of the heating energy when a target temperature rate of change of the target zone is reached.

16. The method of claim 15 wherein automatically adjusting comprises discontinuing delivery of the heating energy to the target tissue.

17. The method of claim 15 wherein the tissue layer is positioned between the plurality of electrodes and the target tissue.

18. The method of claim 15 comprising automatically discontinuing the delivering of the heating energy when a maximum temperature in the target tissue is reached.

19. The method of claim 18 wherein the maximum temperature is between approximately 60° C. to 80° C.

20. The method of claim 15 comprising reducing a power level of the delivering of the heating energy if a maximum temperature is reached and a predetermined minimum treatment time is not reached.

21. The method of claim 20 wherein the minimum treatment time is between approximately 90 seconds to 150 seconds.

22. The method of claim 15 comprising automatically discontinuing the delivering of the heating energy when a temperature equilibrium in the target tissue is reached.

23. The method of claim 15 wherein the plurality of electrodes comprises at least a first, second, and third electrode, wherein continuously monitoring comprises:
  delivering a first energy to the tissue layer to allow for measuring of a difference in tissue electrical impedance between the first/second and second/third electrodes; and
  preventing the delivery of the heating energy to the target zone if the difference in tissue electrical impedance between the first/second electrodes and the second/third electrodes is greater than a predetermined tissue impedance difference.

24. The method of claim 23 wherein the predetermined tissue impedance difference is between approximately 15Ω to 30Ω.

25. The method of claim 23 wherein the first energy is approximately 5 watts.

26. The method of claim 23 wherein the heating energy is between approximately 30 and 50 watts.

27. The method of claim 15 wherein the plurality of electrodes comprise at least a first, second and third electrode, wherein continuously monitoring comprises:
  measuring the maximum impedance of the tissue with a combination of at least one of the first and third electrodes, first and second electrodes, and second and third electrodes; and
  preventing the delivery of the heating energy to the target zone if the tissue electrical impedance measured with the at least one of the first and third electrodes, first and second electrodes, and second and third electrodes is greater than a predetermined maximum tissue impedance.

28. The method of claim 27 wherein the maximum impedance is between approximately 200Ω to 400Ω.

29. The method of claim 15 comprising deploying a temperature probe into the target tissue.

30. A method of therapeutically heating a target zone of a collagenous support tissue within a patient body, the method comprising:
  electronically determining an acceptable or unacceptable contact condition between an energy source and a first tissue layer disposed proximally to the target zone, the energy source comprising a plurality of electrodes, each of the electrode adapted to contact a corresponding region of the first tissue layer,
  the electronically determining further comprising measuring an impedance value of at least one of the first tissue layer and the target zone,
  the measuring comprising causing each of the electrodes to irradiate the first tissue layer with energy at a first power level,
  comparing the impedance values measured with each of the plurality of electrodes, the comparing yielding the unacceptable contact condition determination if each of the impedance values measured with each of the plurality of electrodes is not within a predetermined range of each other,
  the measuring yielding the unacceptable contact condition determination if any of the impedance values exceeds a predetermined maximum impedance level, wherein the determination is made only after the irradiating has occurred for a first predetermined time period;
  upon determining the acceptable contact condition, deploying a temperature probe into the target zone tissue, cooling the first tissue layer and target zone, the cooling causing the temperature of the target zone tissue layer to remain below a first predetermined temperature;
  upon determining the acceptable contact condition, irradiating for a finite time period the target zone with RF energy to cause an increase in target zone temperature to the second predetermined temperature, the irradiating further comprising at least one of:
  i) determining a temperature equilibrium condition of the target zone, the temperature equilibrium condition comprising descent below a predetermined rate change level of a temperature rate of change of the target zone, the irradiating being discontinued after a second predetermined time period from the temperature equilibrium condition determination;
  (ii) determining a third predetermined temperature of the target zone, the irradiating being discontinued if the target zone is determined to have reached the third temperature; and
  (iii) after the irradiating, determining a fourth predetermined temperature of the target zone; and
  after the determining a fourth predetermined temperature, discontinuing the cooling of the first tissue and target zone tissue layers.

31. The method of claim 4 wherein the first predetermined time is 20–60 seconds.

32. A method of therapeutically heating a target zone of a collagenous tissue within a patient body, the method comprising:
  continuously monitoring a contact condition between a tissue layer and a plurality of electrodes;
  delivering a heating energy with the plurality of electrodes to heat the target zone; and
  automatically adjusting the delivering of the heating energy to the target zone if an acceptable contact condition between the tissue layer and at least one electrode is not maintained,
  wherein adjusting the delivery of the heating energy comprises automatically discontinuing the delivering of the heating energy when a predetermined temperature rate of change of the tissue in the target zone is reached.

33. The method of claim 32 wherein automatically adjusting comprises discontinuing delivery of the heating energy to the target tissue.

34. The method of claim 32 comprising automatically discontinuing the delivering of the heating energy when a maximum temperature in the target tissue is reached.

35. The method of claim 34 wherein the maximum temperature is between approximately 60° C. to 80° C.

36. The method of claim 32 comprising reducing a power level of the delivering of the heating energy if a maximum temperature is reached and a predetermined minimum treatment time is not reached.

37. The method of claim 36 wherein the minimum treatment time is between approximately 90 seconds to 150 seconds.

38. The method of claim 32 comprising automatically discontinuing the delivery of heating energy when a maximum treatment time is reached.

39. A method of therapeutically heating a target zone of a collagenous tissue within a patient body, the method comprising:

continuously monitoring a contact condition between a tissue layer and a plurality of electrodes;

delivering a heating energy with the plurality of electrodes to heat the target zone; and automatically adjusting the delivering of the heating energy to the target zone if an acceptable contact condition between the tissue layer and at least one electrode is not maintained, wherein the plurality of electrodes comprises at least a first, second, and third electrode, wherein continuously monitoring comprises:

delivering a first energy to the tissue layer to allow for measuring of a difference in tissue electrical impedance between the first/second and second/third electrodes; and preventing the delivery of the heating energy to the target zone if the difference in tissue electrical impedance between the first/second electrodes and the second/third electrodes is greater than a predetermined tissue impedance difference.

40. The method of claim 39 wherein the predetermined tissue impedance difference is between approximately 15Ω to 30Ω.

41. The method of claim 39 wherein the first energy is approximately 5 watts.

42. The method of claim 39 wherein the heating energy is between approximately 30 and 50 watts.

43. A method of therapeutically heating a target zone of a collagenous tissue within a patient body, the method comprising:

continuously monitoring a contact condition between a tissue layer and a plurality of electrodes;

delivering a heating energy with the plurality of electrodes to heat the target zone; and automatically adjusting the delivering of the heating energy to the target zone if an acceptable contact condition between the tissue layer and at least one electrode is not maintained, wherein the plurality of electrodes comprise at least a first, second and third electrode, wherein continuously monitoring comprises:

measuring the maximum impedance of the tissue layer with a combination of at least one of the first and third electrodes, first and second electrodes, and second and third electrodes; and preventing the delivery of the heating energy to the target zone if the tissue electrical impedance measured with the at least one of the first and third electrodes, first and second electrodes, and second and third electrodes is greater than a predetermined maximum tissue impedance.

44. The method of claim 43 wherein the maximum impedance is between approximately 200Ω to 400Ω.

45. A method of therapeutically heating a target zone of a collagenous tissue within a patient body, the method comprising:

positioning an applicator that comprises a plurality of electrodes against a region of a first tissue layer that is disposed adjacent to the target zone;

determining a uniformity of contact between the plurality of electrodes and the first tissue layer;

upon determining an acceptable uniformity of contact, irradiating the target zone with energy through the plurality of electrodes for a finite time period, and deploying a temperature probe into the target zone to measure a temperature of the target zone temperature and cooling the first tissue layer and target zone, wherein cooling causes the temperature of the target zone to remain below a first predetermined temperature, and upon determining an unacceptable uniformity of contact, causing cessation of the irradiating or preventing irradiating from occurring.

46. The method of claim 45 wherein determining the uniformity of contact comprises measuring an impedance value of at least one of the first tissue layer and the target zone with selected pairings of the plurality of electrodes; and comparing the impedance values measured by the selected pairings of electrodes, wherein the acceptable uniformity of contact occurs if each of the measured impedance values is within a predetermined range of each of the other measured impedance values.

47. The method of claim 46 wherein measuring an impedance value comprises causing each of the electrodes to irradiate the first tissue layer at a first power level.

48. The method of claim 46 wherein comparing the impedance values occurs after the irradiating has been performed for a predetermined time duration.

49. The method of claim 45 wherein the energy comprises RF energy.

50. The method of claim 45 wherein irradiating causes a stiffening or shrinkage of the target zone.

51. The method of claim 45 wherein irradiating further comprises:

measuring a temperature rate of change of the target zone;

comparing the measured temperature rate of change in the target zone with a predetermined rate of change level; and once the measured temperature rate of change descends below the predetermined rate of change level, discontinuing the irradiating after a first predetermined time duration has elapsed.

52. The method of claim 45 further comprising:

measuring a temperature of the target zone with the temperature probe; and upon reaching a predetermined target zone temperature, discontinuing the cooling of the first tissue layer.

53. The method of claim 45 wherein irradiating further comprises automatically discontinuing irradiation when the target zone has reached a predetermined maximum temperature.

54. The method of claim 53 wherein the predetermined maximum temperature is between approximately 60° C. and 80° C.

55. The method of claim 45 wherein irradiating is ceased when a maximum treatment time is reached.

56. A method of therapeutically heating a target zone of a collagenous tissue within a patient body, the method comprising:

monitoring a contact condition between a tissue layer and a plurality of electrodes;

delivering a heating energy through the plurality of electrodes to heat the target zone;

pre-cooling the tissue layer prior to delivering the heating energy;

automatically adjusting the delivering of the heating energy to the target zone if an acceptable contact condition between the tissue layer and at least one electrode is not maintained; and monitoring a temperature of the target zone and automatically discontinuing the delivering of the heating energy when a maximum temperature in the target zone is reached.

57. The method of claim 56 wherein monitoring a contact condition comprises measuring an impedance value of the tissue layer with selected pairings of the plurality of electrodes; and comparing the impedance values measured by the selected pairings of electrodes with each other, wherein the acceptable contact condition occurs if each of the measured impedance values is within a predetermined range of each of the other measured impedance values.

58. The method of claim 57 further comprising measuring a temperature rate of change of the target zone to determine if a target temperature equilibrium condition in the target zone has been reached.

59. The method of claim 56 wherein automatically adjusting the delivering of the heating energy comprises reducing a power level or discontinuing the delivering of energy.

60. The method of claim 56 wherein the maximum temperature is between about 60° C. and 80° C.

61. A method of therapeutically heating a target zone of a collagenous tissue within a patient body, the method comprising:

monitoring a contact condition between a tissue layer and a plurality of electrodes;

delivering a heating energy through the plurality of electrodes to heat the target zone;

pre-cooling the tissue layer prior to delivering the heating energy;

automatically adjusting the delivering of the heating energy to the target zone if an acceptable contact condition between the tissue layer and at least one electrode is not maintained; and monitoring a temperature of the target zone and reducing a power level of the delivering of the heating energy if a maximum temperature in the target zone is reached and a predetermined minimum treatment time is not reached, wherein reducing the power level is sufficient to maintain the temperature of the target zone at the maximum temperature until the minimum treatment time is reached.

62. The method of claim 61 wherein monitoring a contact condition comprises measuring an impedance value of the tissue layer with selected pairings of the plurality of electrodes; and comparing the impedance values measured by the selected pairings of electrodes with each other, wherein the acceptable contact condition occurs if each of the measured impedance values is within a predetermined range of each of the other measured impedance values.

63. The method of claim 61 wherein automatically adjusting the delivering of the heating energy comprises reducing a power level or discontinuing the delivering of energy.

64. The method of claim 61 wherein the plurality of electrodes are cooled, wherein pre-cooling comprises contacting the cooled electrodes against the tissue layer.

65. The method of claim 61 wherein the maximum temperature is between about 60° C. and 80° C.

* * * * *